(12) United States Patent
Kirkpatrick

(10) Patent No.: US 9,980,474 B2
(45) Date of Patent: May 29, 2018

(54) ELASTOMERIC HORSESHOE AND METHOD OF MAKING SAME

(71) Applicant: Sound Horse Technologies, LLC, Unionville, PA (US)

(72) Inventor: William J. Kirkpatrick, West Chester, PA (US)

(73) Assignee: Sound Horse Technologies, LLC, Unionville, PA (US)

( * ) Notice: Subject to any disclaimer, the term of this patent is extended or adjusted under 35 U.S.C. 154(b) by 0 days. days.

(21) Appl. No.: 15/386,721

(22) Filed: Dec. 21, 2016

(65) Prior Publication Data

US 2017/0172133 A1 Jun. 22, 2017

Related U.S. Application Data

(63) Continuation-in-part of application No. 15/290,801, filed on Oct. 11, 2016.

(Continued)

(51) Int. Cl.
*A01L 5/00* (2006.01)
*A01L 3/02* (2006.01)
(Continued)

(52) U.S. Cl.
CPC .................. *A01L 5/00* (2013.01); *A01L 3/00* (2013.01); *A01L 3/02* (2013.01); *A01L 7/02* (2013.01);
(Continued)

(58) Field of Classification Search
CPC ..... A01L 5/00; A01L 3/00; A01L 3/02; A01L 7/02; B29C 39/123; B29K 2055/02;
(Continued)

(56) References Cited

U.S. PATENT DOCUMENTS

| 3,712,872 A | * | 1/1973 | Lammers et al. .... B29C 41/003 |
| | | | 264/310 |
| 3,732,929 A | * | 5/1973 | Glass .................. A01K 13/007 |
| | | | 168/18 |

(Continued)

FOREIGN PATENT DOCUMENTS

| EP | 0832560 A1 * | 4/1998 | ............... A01L 5/00 |
| GB | 1405211 A | 9/1975 | |

(Continued)

*Primary Examiner* — Kathleen I Alker
(74) *Attorney, Agent, or Firm* — Axenfeld Law Group, LLC; Robert R. Axenfeld; Vikram Patel

(57) ABSTRACT

A horseshoe for attaching a non-metallic horseshoe to a horse's hoof using an adhesive is described. In one example, the horseshoe includes a first layer composed of an elastomeric material, which forms a body of the horseshoe. The first layer may extend longitudinally from a ground-facing surface of the horseshoe to a portion of the hoof-facing surface of the horseshoe. A second layer is embedded at least partially in and on the first layer. The second layer forms at least a portion of the hoof-facing surface of the horseshoe. The second layer may include an acrylonitrile butadiene styrene (ABS) material, a polyvinyl chloride (PVC) material, and/or an aluminum powder. Also described is a method of making the elastomeric horseshoe.

4 Claims, 5 Drawing Sheets

Related U.S. Application Data

(60) Provisional application No. 62/270,369, filed on Dec. 21, 2015.

(51) Int. Cl.

| | | |
|---|---|---|
| *B29C 39/12* | (2006.01) | |
| *A01L 3/00* | (2006.01) | |
| *A01L 7/02* | (2006.01) | |
| B29K 75/00 | (2006.01) | |
| B29K 55/02 | (2006.01) | |
| B29K 27/06 | (2006.01) | |
| B29K 105/16 | (2006.01) | |
| B29K 505/02 | (2006.01) | |
| A61B 90/00 | (2016.01) | |

(52) U.S. Cl.
CPC .... *B29C 39/123* (2013.01); *A61B 2090/3966* (2016.02); *B29K 2027/06* (2013.01); *B29K 2055/02* (2013.01); *B29K 2075/00* (2013.01); *B29K 2105/16* (2013.01); *B29K 2505/02* (2013.01)

(58) Field of Classification Search
CPC ............ B29K 2075/00; B29K 2105/16; B29K 2027/06; B29K 2505/02; A61B 2090/3966
See application file for complete search history.

(56) References Cited

U.S. PATENT DOCUMENTS

| | | | | |
|---|---|---|---|---|
| 3,782,473 | A * | 1/1974 | Spencer | A01L 3/00 168/4 |
| 3,907,036 | A * | 9/1975 | Capone | A01L 1/04 168/26 |
| 3,913,679 | A | 10/1975 | Bucalo et al. | |
| 3,999,611 | A * | 12/1976 | Bucalo | A01K 15/02 168/4 |
| 4,287,250 | A * | 9/1981 | Rudy | A43B 13/20 206/522 |
| 4,580,637 | A | 4/1986 | King | |
| 4,605,071 | A * | 8/1986 | McKibben | A01L 5/00 168/12 |
| 4,819,731 | A * | 4/1989 | Stubbe | A01L 5/00 168/12 |
| 4,892,150 | A * | 1/1990 | Thoman | A01L 3/00 168/20 |
| 5,027,904 | A | 7/1991 | Miller et al. | |
| 5,289,878 | A * | 3/1994 | Landi | B29C 65/028 168/12 |
| 5,533,575 | A | 7/1996 | Brown | |
| 5,548,125 | A | 8/1996 | Sandbank | |
| 5,699,861 | A * | 12/1997 | Sigafoos | A01L 3/00 168/12 |
| 6,082,462 | A | 7/2000 | Lyden | |
| 6,883,615 | B2 * | 4/2005 | Coulombe | A01L 7/06 168/14 |
| 7,124,832 | B2 * | 10/2006 | Kelly | A01L 5/00 168/4 |
| 7,810,252 | B2 * | 10/2010 | Stone | A43B 7/1425 156/245 |
| 8,512,616 | B2 * | 8/2013 | Kaufmann | B29C 44/08 264/255 |
| 2003/0037462 | A1 * | 2/2003 | Tanaka | A43B 23/086 36/77 R |
| 2003/0167739 | A1 | 9/2003 | Clark et al. | |
| 2004/0031616 | A1 * | 2/2004 | Moller | A01L 7/02 168/12 |
| 2006/0091695 | A1 * | 5/2006 | MacNeil | B29C 47/0021 296/97.23 |
| 2007/0055359 | A1 | 3/2007 | Messer et al. | |
| 2008/0016841 | A1 | 1/2008 | Llewellyn | |
| 2008/0078562 | A1 * | 4/2008 | Kirkpatrick | A01L 7/00 168/14 |
| 2008/0087442 | A1 | 4/2008 | Cherel et al. | |
| 2009/0127801 | A1 | 5/2009 | Heikkila | |
| 2010/0095641 | A1 * | 4/2010 | Ruetenik | A01K 13/007 54/82 |
| 2010/0294517 | A1 | 11/2010 | Poupard | |
| 2011/0224790 | A1 | 9/2011 | Robinson et al. | |
| 2012/0117818 | A1 * | 5/2012 | Slowik | A43B 7/141 36/44 |
| 2013/0220645 | A1 * | 8/2013 | Kirkpatrick | A01L 7/02 168/12 |
| 2014/0033661 | A1 * | 2/2014 | Ruetenik | B29C 70/66 54/82 |
| 2015/0126099 | A1 * | 5/2015 | Krishnan | B33Y 10/00 451/529 |
| 2015/0352818 | A1 * | 12/2015 | Glotin | B32B 27/12 428/442 |
| 2016/0235192 | A1 * | 8/2016 | Kramer | B29C 65/4865 |
| 2017/0067210 | A1 * | 3/2017 | Gasparovic | E01O 5/20 |

FOREIGN PATENT DOCUMENTS

| | | | | |
|---|---|---|---|---|
| WO | WO 9522252 | A1 * | 8/1995 | ............... A01L 5/00 |
| WO | WO 2014176705 | A1 * | 11/2014 | ............... A01L 1/04 |

* cited by examiner

ELASTOMERIC HORSESHOE AND METHOD OF MAKING SAME

CROSS-REFERENCE TO RELATED APPLICATIONS

This application claims the benefit of U.S. Provisional Application No. 62/270,369 filed 21 Dec. 2015. This application is also a continuation-in-part of prior application Ser. No. 15/290,801 filed 11 Oct. 2016, which is a continuation of application Ser. No. 14/169,133 filed 30 Jan. 2014 now U.S. Pat. No. 9,462,797. The aforementioned applications are fully incorporated herein by reference.

COPYRIGHT NOTICE

A portion of this disclosure or this patent document contains material, which is subject to copyright protection. The copyright owner has no objection to the facsimile reproduction by anyone of the patent document or the patent disclosure, as it appears in the U.S. Patent and Trademark Office patent file or records, but otherwise reserves all copyright rights.

BACKGROUND

Horseshoes, in general, have not changed much in the last 1,000 years. Horseshoes are usually used to protect a horse's hoof when the horse is put to productive or useful work, or engaged in competitive events and hard training. There are many types of horseshoes with most being made of metal—primarily steel or aluminum—and fastened directly to the hoof with nails.

For instance, most farriers will use six to eight nails per shoe, but will not insert a nail beyond the midline thereby allowing the heels of the hoof to move laterally across the horseshoe.

Although the vast majority of horseshoes are still applied with nails, more recently, in the last 30 years, progress has been made in successfully fastening metal horseshoes—generally aluminum—to the hoof using glue. Directly gluing horseshoes to a horse's hoof may become necessary for a horse, which has a damaged hoof—broken, cracked, thin, brittle or shelly.

However, a potential drawback with directly gluing a horseshoe to horse's hoof is that the horseshoe is glued to the entire hoof perimeter beyond the midline to generate an adequate bond strength. Keep in mind, that a horse typically weighs over a 1,000 lbs. and can run over 30 mph, cut at 45°, and jump over a five-foot object. This is why the horseshoe is usually glued to the entire perimeter of the hoof. Otherwise, if the horseshoe is not adequately bonded to the hoof, it will either fall off the hoof, become dislodged or loose, and may injure the horse and its rider.

But gluing the entire hoof perimeter past the midline to the horseshoe has drawbacks. For instance, if the heels of the horse's hoof are glued to the shoe, the heels cannot laterally expand and contract as it loads and unloads, and will not naturally bio-mimic the action of an unconstrainted hoof. Thus, gluing the heels of a horse's hoof to the horseshoe is often counterproductive, because the heel cannot move naturally on the heel of the horseshoe, often resulting in lameness, pain and soreness to an already sore or damaged hoof.

Another drawback with aluminum horseshoes, is that they don't offer shock attenuation. This can result in aggravating soreness in the horse's hoof. And although aluminum shoes are generally lighter than steel horseshoes, aluminum shoes are about 40% heavier than plastic horseshoes.

That is why many farriers select plastic horseshoes (i.e., urethane or polyurethane) over aluminum or steel. Put differently, a well-designed plastic horseshoe offers substantial shock attenuation over steel or aluminum horseshoes. In addition, plastic horseshoes are about 70% lighter than steel shoes, and are almost half as light as aluminum. Many plastic shoes also offer adequate support and grip to the horse, when it performs work.

But plastic horseshoes suffer from many of the same problems as aluminum shoes when it comes to attaching the horseshoe to directly the horse's hoof using adhesive bonding. That is, like aluminum shoes, plastic horseshoes are often applied to horse's hoof in a non-traditional manner by "glueing" the shoe directly to the bottom of the horse's hoof without any nails. Farriers may trim the hoof, shape the shoe, and then apply to the hoof wall with an adhesive. Two potential common adhesives may be used to attach the horseshoe to the hoof: (1) urethane adhesive, or (2) an acrylic adhesive.

While urethane adhesives grab a urethane-based horseshoe quickly and reliably, farriers generally prefer to use acrylic adhesives—such as a methyl-methacrylate—because it tends to generate a more reliable bond between a horse's hoof and the horseshoe than a urethane adhesive.

That is, methacrylate adhesives are more robust than urethane adhesives. For instance, methacrylate adhesives tolerate more surface contamination and a bit more moisture in the hoof than urethane adhesive do. This is why farriers and equine vets—who work in less than clean environments when shoeing, and can't easily control the bond-surface condition—prefer methacrylate adhesives over urethanes.

Although methacrylate adhesives will bond well to a hoof (an organic material) it generates varying bonding strengths depending on the chemistry of the plastics the methacrylate is attempting to "grab" (i.e., bond to). This may result in plastic horseshoes that are not effectively bonded to the horse's hoof, and may fall off, or become partially dislodged, which can injure a horse or its rider.

To avoid this problem, most farriers glue the heels of the hoof to the plastic horseshoe to achieve a total overall higher bonding strength, because more surface area generally equals higher strength with adhesives. Again, this negatively constrains the natural movement of a horse's hoof, and may result in heel bruises as a result.

There are other problems with plastic horseshoes. For instance, many new plastic horseshoes, which are injection molded are only available in a limited number of shapes and sizes; most likely due to the high cost of producing an injection die for each size and each shape of horseshoe. Thus, plastic horseshoes that are injection molded are usually expensive, and not readily available in different shapes and sizes, due to expense.

Further, because injection molding produces a part that is thermos-plastic, the horseshoe is not highly resistant to abrasion. This may result in a horseshoe that wears prematurely or unevenly.

SUMMARY

This document describes an elastomeric horseshoe and method of making same. The horseshoe is cast or printed rather than injection molded.

In one aspect, the horseshoe includes a first layer composed of an elastomeric material, which forms a body of the horseshoe. The first layer may extend longitudinally from a ground-facing surface of the horseshoe to a portion of the hoof-facing surface of the horseshoe. A second layer is embedded at least partially in and on the first layer, usually during the casting process. The second layer forms at least a portion of the hoof-facing surface of the horseshoe. The second layer may include an acrylonitrile butadiene styrene (ABS) material, a polyvinyl chloride (PVC) material, and/or an aluminum powder.

Reference in this document to an "embodiment", "aspect", "example" or "implementation" means that a particular feature, structure, method or characteristic described in connection with that "embodiment" "aspect" "example" or "implementation" is included in the document. However, the appearances of such phrases or formulations are not necessarily all referring to the same "embodiment", "aspect", "example" or "implementation." Furthermore, various particular features, structures, operations, or characteristics may be combined in any suitable manner in one or more "embodiment", "aspect", "example" or "implementation."

As used this document, the term "horse" refers to any hoofed animal in the equine family or others that may wear shoes that attach to their hoofs, such as a horse, pony, donkey mule or other animals having keratinous hoof materials.

This Summary is provided to introduce a selection of concepts in a simplified form that are further described below in the Detailed Description. This Summary is not necessarily intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components. The figures are not necessarily drawing to scale, and for illustration purposes only.

DETAILED DESCRIPTION

Figure 1:
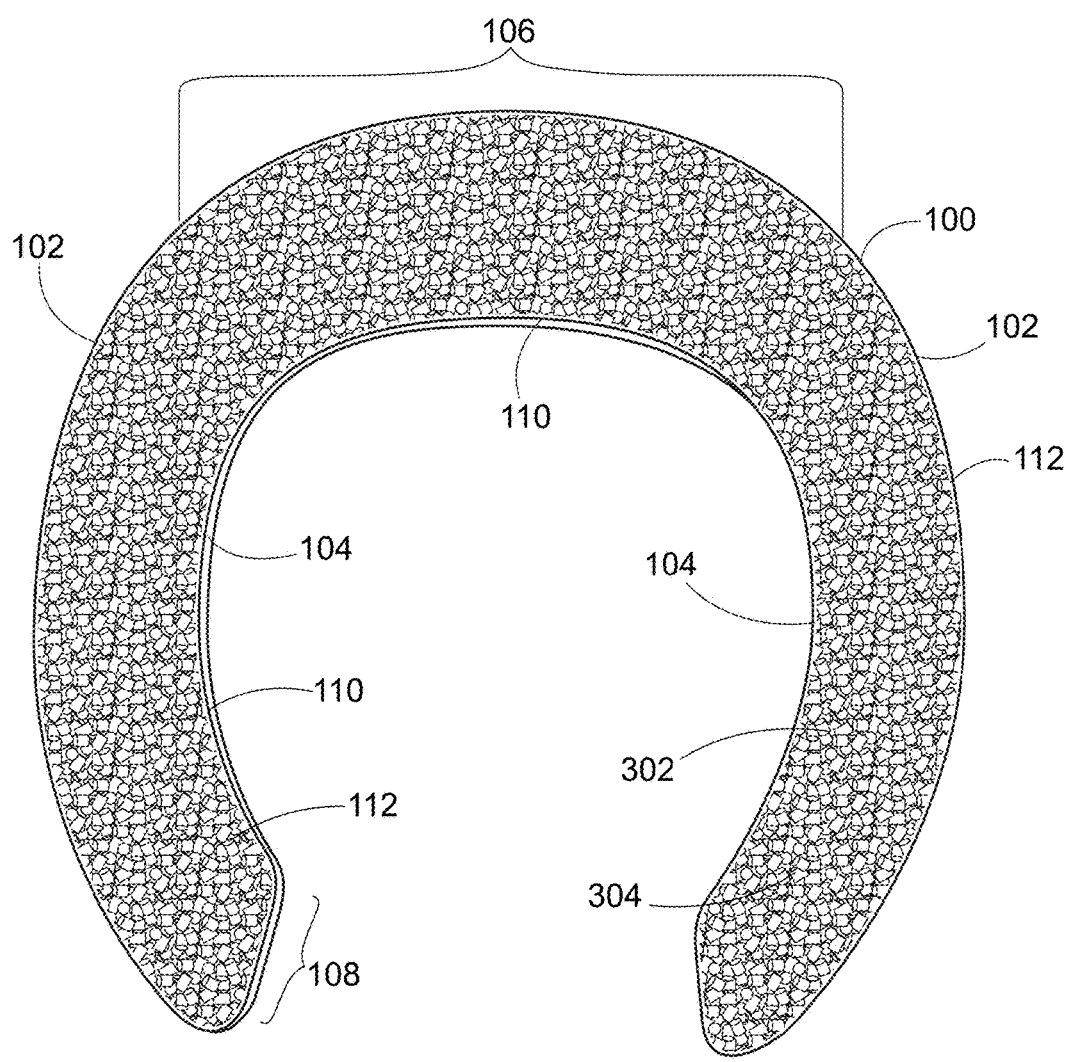
FIG. 1 shows a top view (hoof-facing view) of an example elastomeric horseshoe.

FIG. 1 shows a top view (hoof-facing view) of an example elastomeric horseshoe 100. Horseshoe 100 may include an outer edge 102, an inner edge 104, a toe 106, and a heel portion 108. The outer edge 102, inner edge 104, and toe 106 (at the periphery) collectively form a peripheral sidewall 110 of horseshoe 100 that is coextensive along the periphery of horseshoe 100. In other words, peripheral sidewall 110 traces the outline boundaries of, in this example, a U-shaped horseshoe 100.

Also, depicted in FIG. 1, a hoof-facing surface 112 is configured to bonds with a horse's hoof (not shown). Potential layer(s) of material for use with hoof-facing surface 112, and placement of these materials will be described in more detail below.

Figure 2:
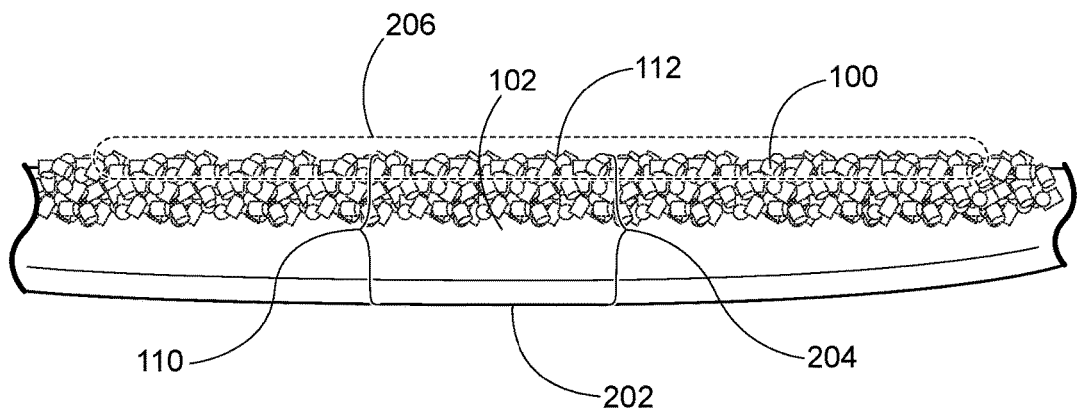
FIG. 2 shows a left-side view of example horseshoe shown in FIG. 1.

FIG. 2 shows a left-side view of example horseshoe 100 shown in FIG. 1. As depicted in FIG. 2, a first layer 204 of elastomeric material extends longitudinally from a ground-facing surface 202 of horseshoe 100 to hoof-facing surface 112 including encompassing peripheral sidewall 110. That is, ground-facing surface 202 and peripheral sidewall 110 are constructed of a first layer 204 of material such as rugged thermoset-urethane material. However, as appreciated by those skilled in the relevant art, the elastomeric material may include any suitable urethane or polyurethane material capable of being cast in a desired-horseshoe shape and size.

Put differently, first layer 204 of material extends externally along peripheral sidewall 110, from ground-facing surface 202 to a portion 206 of hoof-facing surface 112 that runs substantially along a top portion of each outer edge 102 (see also FIG. 1) and inner edge 104 (see also FIG. 1) of horseshoe 100. Thus, first layer 204 of material forms an external encasement of horseshoe 100, including ground-facing surface 202, and extends along externally along peripheral sidewall 110 to a portion 206 of hoof-facing surface 112. In other words, first layer 204 encases the bottom (ground-facing surface 202) and peripheral sidewalls 110 of horseshoe 100 with a rugged thermoset urethane material.

In another aspect, first layer 204 also serves as the foundation or internal body of horseshoe 100. For instance, FIG. 3 shows a cross-sectional view of the same left-sided view of example horseshoe 100 shown in FIG. 2.

Figure 3:
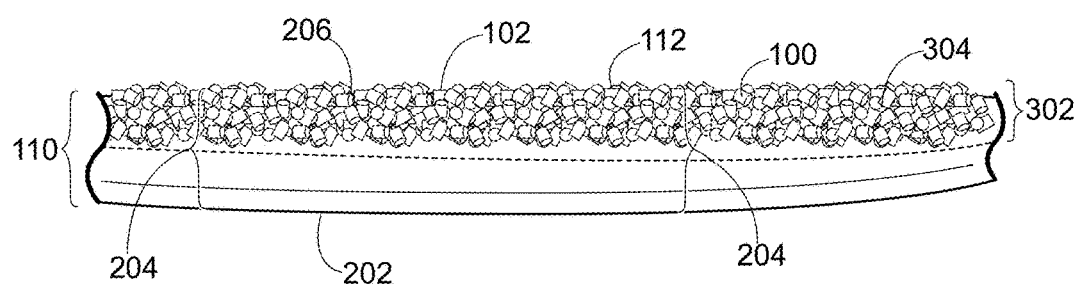
FIG. 3 shows a cross-sectional view of the same left-sided view of example horseshoe shown in FIG. 2.

As depicted in FIG. 3, first layer 204 of material viewed centrally inside horseshoe 100, serves as foundation for a second layer 302 of material to reside. That is, second layer 302 of material is embedded at least partially in, and/or secured on top of first layer 204 of material. Second layer 302 of material forms at least a portion of hoof-facing surface 112 (see also FIG. 1).

Second layer 302 may encompasses between about 5% and 30% of the overall height of horseshoe 100 measured longitudinally inside (central area) horseshoe from ground-facing surface 202 to hoof-facing surface 112. As appreciated by those skilled in the art, the exact percentage of overall height of that second layer 302 may occupy in horseshoe 100 may be greater than 30% or less than 5%.

In addition, second layer 302 may encompass between about 5% and 25% of a total quantity of materials comprising horseshoe 100. As appreciated by those skilled in the art, the exact percentage of the quantity of material that second layer 302 may occupy in horseshoe 100 may be greater than 25% or less than 5%.

In one aspect, second layer 302 of material is an acrylonitrile butadiene styrene (ABS) material. For instance, as depicted in FIGS. 1 and 3, second layer 302 may include a plurality of ABS pellets 304 approximately 1/16 to 1/8 of inch thick. Of course, the size of pellets 304 may be slightly bigger or smaller. In addition, the shape of pellets 304 may vary.

In another aspect, second layer 302 of material is a polyvinyl chloride (PVC) material. For instance, second layer 302 may include a plurality of PVC pellets (not shown, but generally the same shape as ABS pellets 304) approximately 1/16 of inch thick. Of course, the size of the pellets may be slightly bigger or smaller.

In still another aspect, second layer 302 of material is an aluminum powder or dust. In addition, second layer 302 may also include aluminum grindings or pellets of various sizes and shapes.

In still another aspect, second layer 302 may include any combination of ABS, PVC and Aluminum dust.

As an alternative to using a plurality of pellets, second layer 302 may also include a solid plate or sheet of material of an suitable shape and dimensions (not shown) made of ABS, PVC and/or Aluminum to serve as a hoof-facing surface 112. Similar to pellets or dust, a solid plate may be embedded or otherwise integrated with first layer 204.

If second layer 302 is primarily a plurality of ABS pellets 304, hoof-facing surface 112 will increase the bond strength a factor of four or five times over simply attempting to bond directly to an elastomeric material such as a urethane or polyurethane horseshoe.

If second layer 302 is primarily a plurality of PVC pellets, hoof-facing surface 112 will increase the bond strength a factor of seven times over simply attempting to bond directly to an elastomeric material such as a urethane or polyurethane horseshoe.

If second layer 302 is primarily aluminum dust, hoof-facing surface 110 will increase the bond strength a factor of greater than seven times over simply attempting to bond directly to an elastomeric material such as a urethane or polyurethane horseshoe.

Referring back to FIG. 1, second layer 302 is shown as a plurality of PVC pellets integrated on and in first layer 204 (shown in FIGS. 2 and 3). That is, as depicted in FIG. 1, second layer 302 spans a majority of a coplanar area of hoof-facing surface 112 between inner edge 104 and outer edge 102 of horseshoe 100. Some portions of second layer may also extend to perimeter edges of horseshoe 100, and overlap with first layer 204 along these perimeter edges (i.e. inner edge 104 and outer edge 102).

As appreciated by those skilled in the art, second layer 302 may not encompass all planar areas of hoof-facing surface 112. That is second layer 302 may not be disposed on all portions of hoof-facing surface 112, such as heel 108.

Horseshoe 100 may be made different ways. For instance, in one aspect, a first layer 204 of material is poured into an open cast mold (not shown) of a horseshoe. Then second layer 302 of material is deposited on to the first layer of material, and then allowing curing of first layer 204.

For example, ABS pellets, PVC pellets, and/or aluminum dust (or solid plates of these materials) may be deposited on a pre-cured (recently poured) first layer 204 of urethane material. These ABS pellets, PVC pellets, and/or aluminum dust (second layer 302) are then embedded in first layer 204, and also occupy a strata (or layer) on top of horseshoe 100 that is depicted as hoof-facing surface 110 (shown as second layer 302) in FIG. 1 viewed from the top.

Figure 4:
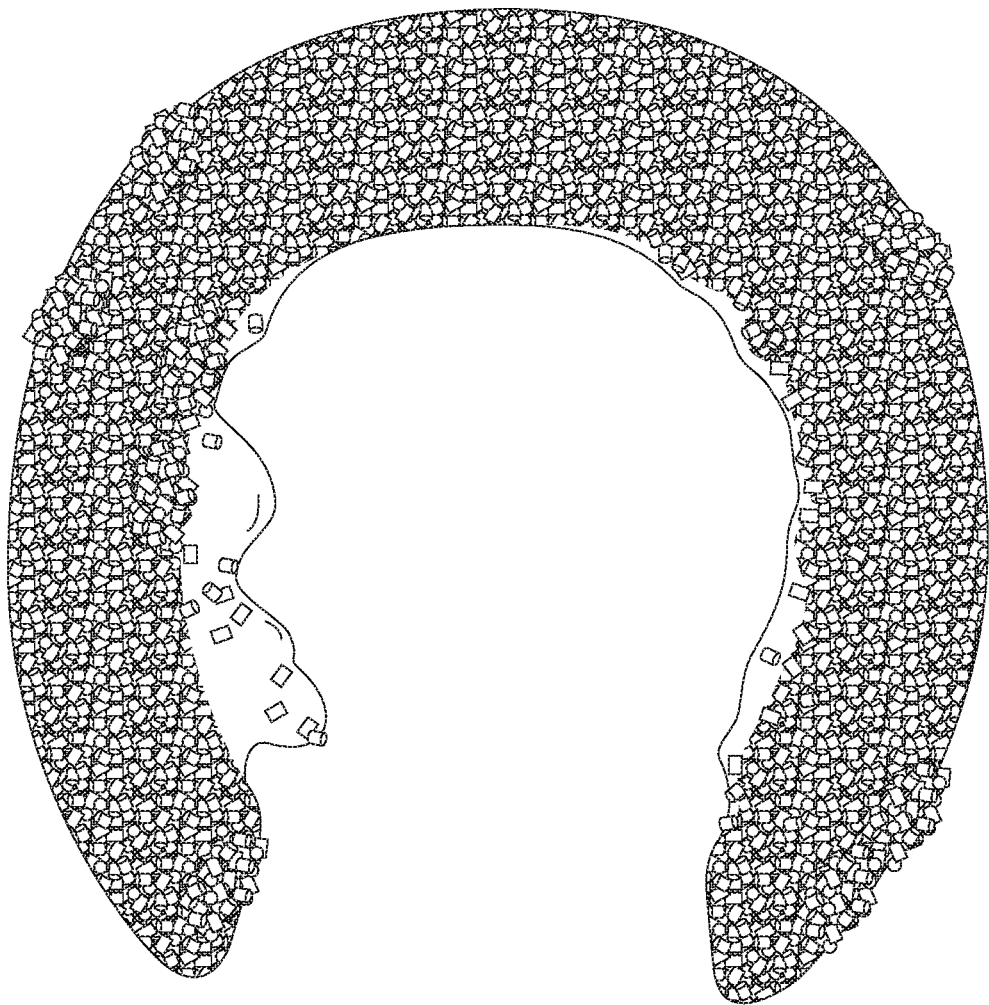
FIG. 4 shows a top view of a horseshoe before sanding hoof-facing surface, and trimming.
Figure 5:
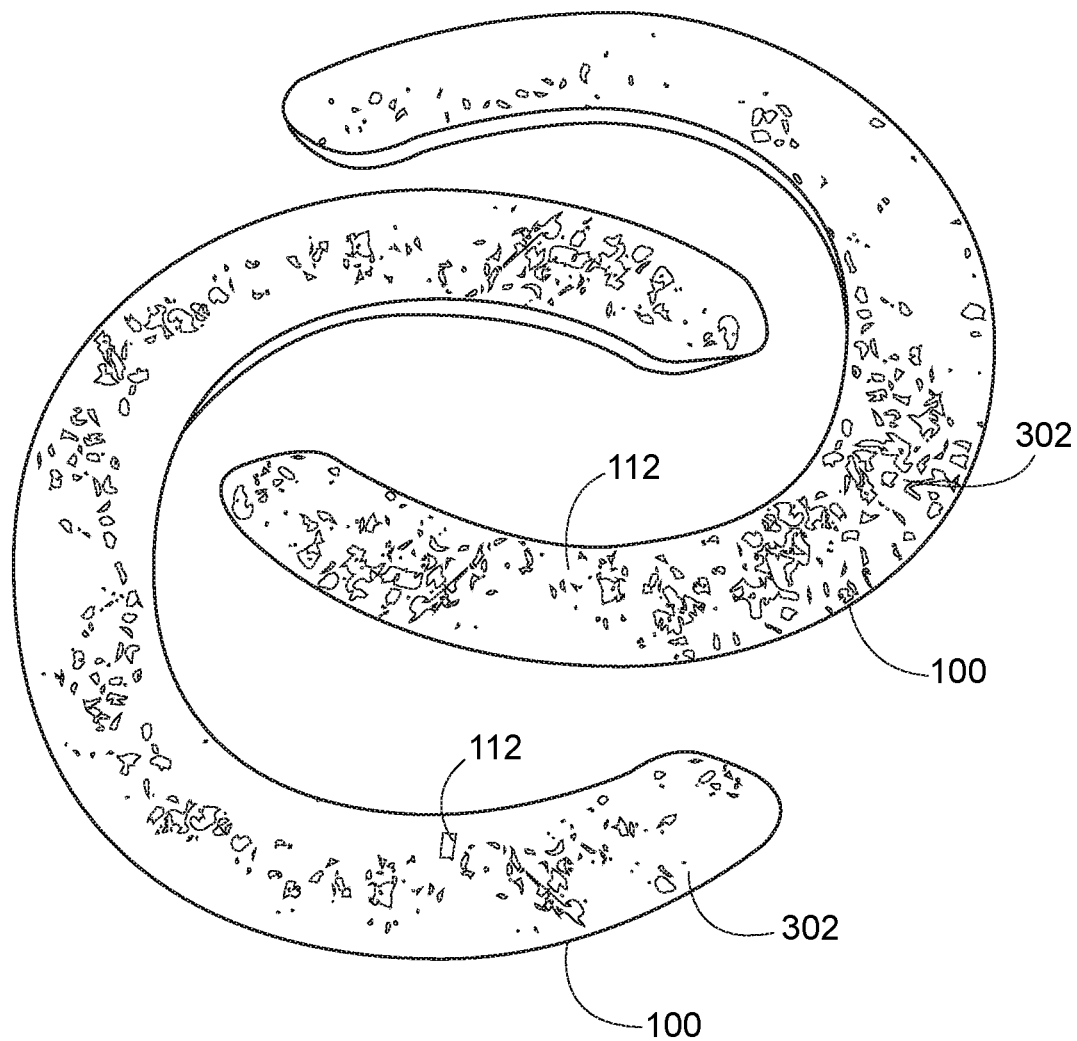
FIG. 5 shows a top view of a horseshoe after sanding hoof-facing surface (including second layer of material), and trimming.

After the second layer 302 is added to first layer 204, and permitted to cure at approximately 16 hours and heated at approximately 180 degrees Fahrenheit, horseshoe 100 is trimmed, and hoof-facing surface 112 may be sanded. FIG. 4 shows a top view of horseshoe 100 before sanding, and trimming FIG. 5 shows a top view of horseshoe 100 after sanding and trimming.

Sanding the hoof-facing surface 112 (see FIG. 5) also further exposes second layer 302 for better adhesion-bonding strength when adhered to a hoof using an adhesive, such as a methacrylate adhesive. Put differently, sanding hoof-facing surface 112 (see FIG. 5), and in particular second layer 302, levels hoof-facing surface 112 of horseshoe 100, controls dimensions, and exposes a maximum surface area of the added bonding material (i.e., second layer 302). Also, the heating and curing process further embeds (i.e. anchors) at least a portion, or more of the second layer 302 of material into, or on first layer 204 of material.

Alternatively, horseshoe 100 may also be three-dimensionally printed.

Still further, as appreciated by those skilled in the art, other materials may be added to the urethane during the manufacturing process, such as a shaping wire or plate as described in U.S. Pat. No. 9,462,797 to Kirkpatrick incorporated herein by reference. In addition, wear material may be added in stratified formation also as described in U.S. Pat. No. 9,462,797.

Although the subject matter has been described in language specific to structural features and/or methodological operations, it is to be understood that the subject matter defined in the appended claims is not necessarily limited to the specific features or operations described. Rather, the specific features and acts are disclosed as example forms of implementing the claims.

What is claimed is:

1. A horseshoe, comprising:
a first layer composed of a thermoset urethane material, wherein the first layer forms a U-shaped body of the horseshoe and includes a peripheral sidewall forming an outwardly-curved outer edge, an inwardly-curved inner edge, and a toe of the horseshoe, wherein the peripheral sidewall extends longitudinally from a ground-facing surface of the horseshoe to a hoof-facing surface of the horseshoe, the ground-facing and hoof-facing surfaces forming outermost surfaces of the horseshoe and the peripheral sidewall forms a first portion of the hoof-facing surface along portions of the outwardly-curved outer edge and the inwardly-curved inner edge; and
a second layer forming a second portion of the hoof-facing surface of the horseshoe that is a central area of the hoof-facing surface surrounded by the outwardly-curved outer edge and the inwardly-curved inner edge, wherein the second layer is embedded at least partially in and on the first layer at an interface, wherein the second layer consists of a plurality of acrylonitrile butadiene styrene (ABS) pellets, the ABS pellets having shapes collectively forming an uneven line at the interface.

2. The horseshoe of claim 1, wherein a central portion of the first layer is located between the outer edge and the inner edge of the shoe, and is substantially covered by the second layer along the hoof-facing surface.

3. The horseshoe of claim 1, wherein the second layer encompasses between about 5% and 30% of the overall height of the horseshoe measured longitudinally from a central area of the ground-facing surface to the central area of the hoof-facing surface.

4. The horseshoe of claim 1, wherein the ABS material consists of a plurality of ABS pellets, in which each ABS pellet is generally between an eighth of an inch and sixteenth of an inch thick.

* * * * *